US009850479B2

(12) United States Patent
Sunner et al.

(10) Patent No.: US 9,850,479 B2
(45) Date of Patent: Dec. 26, 2017

(54) METHOD AND APPARATUS FOR SAMPLING MACROMOLECULES FROM A BIOLOGICAL SPECIMEN

(71) Applicant: The Board of Regents of the University of Oklahoma, Norman, OK (US)

(72) Inventors: Jan Sunner, Norman, OK (US); Iwona Beech, Norman, OK (US); Matthew Kowalski, Edmond, OK (US); Kathleen Duncan, Norman, OK (US); Joseph Suflita, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 15/059,497

(22) Filed: Mar. 3, 2016

(65) Prior Publication Data
US 2016/0257949 A1     Sep. 8, 2016

Related U.S. Application Data

(60) Provisional application No. 62/127,618, filed on Mar. 3, 2015.

(51) Int. Cl.
C12M 1/00 (2006.01)
C12N 15/10 (2006.01)
C12Q 1/68 (2006.01)
G01N 21/71 (2006.01)

(52) U.S. Cl.
CPC ....... C12N 15/1003 (2013.01); C12Q 1/6806 (2013.01); G01N 21/718 (2013.01)

(58) Field of Classification Search
CPC ............. C12Q 1/68; H01J 49/26; A61B 18/18
See application file for complete search history.

(56) References Cited

U.S. PATENT DOCUMENTS

| | | | | |
|---|---|---|---|---|
| 6,111,251 A | * | 8/2000 | Hillenkamp | H01J 49/164 250/288 |
| 6,504,150 B1 | * | 1/2003 | Verentchikov | H01J 49/164 250/281 |
| 6,825,477 B2 | | 11/2004 | Sunner et al. | |
| 8,338,092 B2 | * | 12/2012 | Hofmann | A61L 2/0011 435/6.1 |

OTHER PUBLICATIONS

Kaufman et al, Electric-field-enhanced collection of laser-ablated materials onto a solvent bridge for electrospray ionization mass spectrometry, 2013, Rapid Commun. Mass Spectrom., 27, 1567-1572.*
Brown et al., "Current Techniques for Single-Cell Lysis," J. R. Soc. Interface, 2008, 5:S131-S138.
Chomczynski et al., "Alkaline Polyethylene Glycol-Based Method for Direct PCR from Bacteria, Eukaryotic Tissue Samples, and Whole Blood," Biotechniques, 2006, 40(4):454-458.
Dhawan et al., "Development of a Laser-Induced Cell Lysis System," Anal Bioanal Chem, 2002, 374:421-426.
Hynes et al., "PCR Amplification of Streptococcal DNA Using Crude Cell Lysates," FEMS Microbiology Letters, 1992, 94:139-142.
Karas et al., "Matrix-Assisted Ultraviolet Laser Desorption of Non-Volatile Compounds," International Journal of Mass Spectrometry and Ion Processes, 1987, 78:53-68.
Kephart et al., "A Maximum Instrument at a Minimum Size," www.promega.com, 2006, 92:20-23.
Lin et al., "Cell Lysis Methods for High-Throughput Screening or Miniaturized Assays," Biotechnol. J., 2009, 4:210-215.
Ovchinnikova et al., "Transmission Geometry Laser Ablation into a Non-Contact Liquid Vortex Capture Probe for Mass Spectrometry Imaging," Rapid Commun. Mass Spectrom., 2014, 28:1665-1673.
Radstrom et al., "Pre-PCR Processing," Molecular Biotechnology, 2004, 26:133-146.
Rau et al., Pulsed Laser Microbeam-Induced Cell Lysis: Time-Resolved Imaging and Analysis of Hydrodynamic Effects, Biophysical Journal, 2006, 91:317-329.
Scrhader et al., "PCR Inhibitors—Occurrence, Properties and Removal," Journal of Applied Microbiology, 2012, 113:1014-1026.
Tanaka et al., "Protein and Polymer Analyses up to m/Z 100 000 by Laser Ionization Time-of-Flight Mass Spectrometry," Rapid Communications in Mass Spectrometry, 1988, 2(8)151-153.
Wilson, "Inhibition and Facilitation of Nucleic Acid Amplification," Applied and Environmental Microbiology, 1997, 63 (10):3741-3751.
Zoetendal et al., "DNA Isolation Protocols Affect the Detection Limit of PCR Approaches of Bacteria in Samples from the Human Gastrointestinal Tract," System Appl. Microbiol., 2001, 24:405-410.
Park et al., "Infrared Laser Ablation Sample Transfer for MALDI and Electrospray," J. Am. Soc. Mass Spectru, 2011, 22:1352-1362.
Nelson et al., "Volatilization of High Molecular Weight DNA by Pulsed Laser Ablation of Frozen Aqueous Solutions," Reports, 1989, 1585-1587.
Capizzi et al., "Microbiologic Activity in Laser Resurfacing Plume and Debris," Lasers in Surgery and Medicine, 1998, 23:172-174.
Baggish et al., "Presence of Human Immunodeficiency Virus DNA in Laser Smoke," Lasers in Surgery and Medicine, 1991, 11:197-203.
Schieltz et al., "Mass Spectrometry of DNA Mixtures by Laser Ablation From Frozen Aqueous Solution," Rapid Communication in Mass Spectrometry,1992, 6:631-636.

* cited by examiner

*Primary Examiner* — Narayan Bhat
(74) *Attorney, Agent, or Firm* — Eversheds Sutherland (US) LLP

(57) ABSTRACT

Apparatus and methods for laser ablation sampling, electrophoretic extraction from the laser plume, electrophoretic transport to a container, and capture of macromolecules of interest. In certain embodiments, when macromolecules of interest are nucleic acid, the apparatus and methods further provides for nucleic acid amplification and detection in a rapid mobile platform for environmental and clinical identification of pathogens.

20 Claims, 8 Drawing Sheets

LANAR Aspiration Interface I

METHOD AND APPARATUS FOR SAMPLING MACROMOLECULES FROM A BIOLOGICAL SPECIMEN

CROSS-REFERENCE TO RELATED APPLICATIONS

This application claims priority to U.S. Provisional Application Ser. No. 62/127,618, filed Mar. 3, 2015, entitled "Method and Apparatus for Sampling Macromolecules from a Biological Specimen", the entire contents of which is incorporated by reference herein.

BACKGROUND

The presently disclosed inventive concepts relate generally to biological and environmental specimen sampling of macromolecules of interest and capture into a receiving device, e.g., a container or plate, for subsequent analysis, more particularly to laser-ablation-based sampling methods and devices, and specifically, to the sampling and analysis of macromolecules, such as nucleic acids, proteins and small peptides.

Rapid identification of harmful microorganisms (including human and animal pathogens) is of paramount importance to public health, national security and environmental safety. Most of the currently used methods rely on DNA recovery and polymerase chain reaction (PCR) amplification of selected DNA regions. The yield and quality of recovered DNA, as well as the presence of any PCR inhibitors, is of critical importance for the success of this approach. They vary considerably with DNA extraction procedures. Thus, the success of PCR-based methods for microbial identification is critically dependent on the DNA extraction strategy selected. Good-quality DNA is required to ensure clean PCR product sequences. Thus, a successful extraction method maintains the quality of DNA throughout the recovery process and minimizes the co-extraction of any compounds that inhibit the PCR. Currently used DNA recovery procedures can be time-consuming and often require a large quantity of starting material.

DNA isolation and purification protocols customized for different types of clinical (blood, tissue, saliva, urine, surface swabs) and environmental (soil, water, waste, sediments) specimens are available and often provided in a pre-packaged kit form. A step common to all DNA recovery methods is the disruption of cellular structures, followed by separation and purification of the DNA from the lysed material. Cell lysis can be achieved through a multitude of single or combined chemical and mechanical means, including enzymatic digestion, bead beating, sonication, application of detergents and solvents, as well as freezing and thawing[1]. Subsequent DNA purification steps may include centrifugation, filtration, selective adsorption on silica, or paramagnetic-particle technology[2]. With the latter system, DNA can be extracted from up to 16 samples in less than 45 minutes. Of major concern are method- and cell type-dependent differences in the efficacy of DNA recovery and, subsequently, its yield. For example when treated with an alkaline polyethyleneglycol, DNAzol® Direct[3], which is also marketed as an universal agent for direct PCR (Molecular Research Center Inc., Cincinnati, Ohio), Gram-negative bacteria are lysed after approximately 15 minutes, while more resistant Gram-positive organisms may require up to 3 hours of incubation at room temperature to achieve cell disruption. This may result in variations in DNA recovery within samples that can result in incorrect information on microbial community structure, particularly in specimens harboring highly diverse populations, such as biofilms[4]. Furthermore, a large variety of compounds inhibit PCR[5]. The specimen itself can be a source of PCR-inhibiting compounds[6], and it is essential that such compounds are removed during DNA sampling and extraction. However, it should be noted that successful PCR is sometimes possible without cleanup of lysates[7].

Undoubtedly, strategies that would rapidly, i.e. within seconds, generate DNA that is ready for PCR amplification are of considerable interest to the life science community[8]. Owing to their unprecedented speed of collecting material from well-defined surface areas, laser ablation-based methods carry great promise for enabling such technology. Applying laser pulses to rapidly deposit a large amount of energy into biological materials and other organic substrates has been explored in a range of important applications across many scientific disciplines. For example, nanosecond, visible or ultraviolet, laser pulses have been employed to disrupt cells[9,10]. Such "optical lysis" has been found to be particularly useful for rupturing single cells[11]. Pulsed laser irradiation is a key step in matrix-assisted laser desorption ionization (MALDI) of biomolecules allowing their analysis with mass spectrometry[12,13].

BRIEF DESCRIPTION OF THE DRAWINGS

Several embodiments of the presently disclosed inventive concepts are hereby illustrated in the appended drawings. It is to be noted however, that the appended drawings only illustrate several typical embodiments and are, therefore, not intended to be considered limiting of the scope of the presently disclosed inventive concepts. Further, in the appended drawings, like or identical reference numerals or letters may be used to identify common or similar elements and not all such elements may be so numbered. The figures are not necessarily to scale and certain features and certain views of the figures may be shown as exaggerated in scale or in schematic in the interest of clarity and conciseness. The bore dimensions shown in the figures are not limited to those shown therein and are only intended to be exemplary.

FIG. 3A is an overview of a mid-IR 2.94 μm laser ablation spot (white arrow), from a deposited suspension of *Desulfoglaeba alkanexedens* on Si. FIG. 3B is a close-up view of irradiated *D. alkanexedens* cells within the ablation spots in FIG. 3A; FIGS. 3C and 3D show *Bacillus licheniformis* cells, surrounded by media residue after IR laser irradiation.

FIG. 5A shows computer-generated top-view composite image of 20 separate stereomicroscope images obtained at different depths. FIG. 5B shows 3-dimensional contours of the holes generated from the same image data as was used for FIG. 5A.

DETAILED DESCRIPTION

Figure 1:
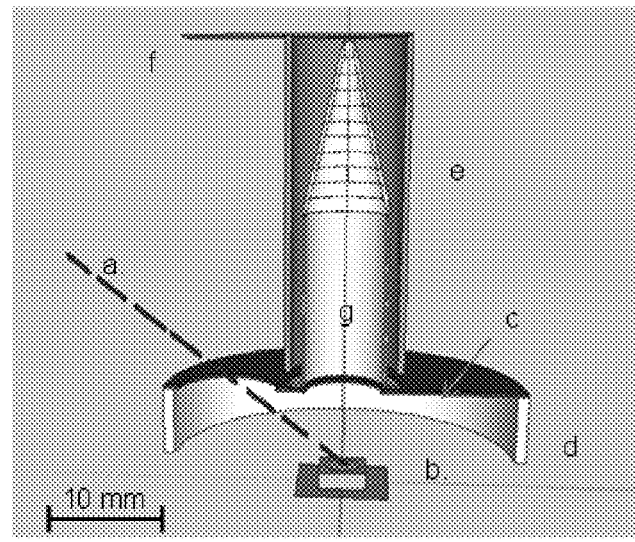
FIG. 1 is a sectional view of an exemplary Laser Ablation for Nucleic Acid Recovery (LANAR) apparatus; a) path of incident, pulsed laser beam; b) substratum (substrate electrode) with a loaded sample; c) "extraction electrode"; d) cylindrical "shielding skirt"; e) tubular "focusing electrode"; f) electrical connection post for focusing electrode; and g) 0.5 mL PCR tube.

The presently disclosed inventive concepts are directed to a method and apparatus for sampling, extracting, and capturing analyte macromolecules of interest, such as nucleic acids and proteins, from a biological specimen. The disclosure includes the processes and devices for sampling a volume of material, including the macromolecules of interest, from the biological specimen in a gaseous ablation plume, extraction of the macromolecules from the ablation plume, separation from matrix material in the plume, and capture of the macromolecules for further detection and analysis. The apparatus can also include a component for identification of the macromolecule, such as a rapid, mobile polymerase chain reaction (PCR) unit, where the analyte macromolecule is a nucleic acid.

Before further describing various embodiments of the presently disclosed inventive concepts in more detail by way of exemplary description, examples, and results, it is to be understood that the presently disclosed inventive concepts are not limited in application to the details of methods and compositions as set forth in the following description. The presently disclosed inventive concepts are capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the presently disclosed inventive concepts may be practiced without these specific details. In other instances, features which are well known to persons of ordinary skill in the art have not been described in detail to avoid unnecessary complication of the description. All of the compositions and methods of production and application and use thereof disclosed herein can be made and executed without undue experimentation in light of the present disclosure.

All patents, published patent applications, and non-patent publications mentioned in the specification are indicative of the level of skill of those skilled in the art to which the presently disclosed inventive concepts pertain. All patents, published patent applications, and non-patent publications referenced in any portion of this application are herein expressly incorporated by reference in their entirety to the same extent as if each individual patent or publication was specifically and individually indicated to be incorporated by reference.

Unless otherwise defined herein, scientific and technical terms used in connection with the presently disclosed inventive concepts shall have the meanings that are commonly understood by those having ordinary skill in the art. Further, unless otherwise required by context, singular terms shall include pluralities and plural terms shall include the singular.

As utilized in accordance with the methods, compositions, and components of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and exemplary claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the term "macromolecule" means one or more molecules of any chemical class, with a molecular weight of at least 1,000 Daltons. In certain embodiments, macromolecules of interest are selected from conventional biopolymers such as nucleic acids, proteins, and carbohydrates, or non-polymeric molecules with large molecular weight such as lipids and macrocycles. In certain embodiments, the macromolecules are single or double stranded nucleic acids (DNA or RNA) of five or more nucleotide bases, or base pairs. For reference, the molecular weight of a double-stranded DNA molecule is approximately equal to the number of base pairs times an average of 650 Daltons/ base pair. The nucleic acids may be naturally occurring, modified, recombinantly expressed or synthetic. In certain embodiments, the macromolecules possess an electric charge (positive or negative), or a charge can be imparted thereto, to facilitate extraction in an electric field. In certain embodiments, macromolecules are associated with other molecules (such as $H_2O$) and the combined entity (cluster) possesses the electric charge (positive or negative) for at least partial separation from some of the plume matrix materials by the use of electric fields.

As used herein, the term "sampling" or "sample" means to the process of removing at least some of the analyte macromolecules from at least some of the biological specimen within which the macromolecules are found. Sampling macromolecules can be achieved, for example, by applying a beam of photons, such as with the use of a continuous or pulsed laser, to the biological specimen to form an ablation plume containing partially isolated macromolecules of interest, as described in more detail below. Alternatively, sampling macromolecules from biological specimen can be achieved by other forces, such as administering shockwaves or heat, or negative (vacuum) or positive air pressure.

As used herein, the term "extracting" or "extract" refers to the process of removing at least some of the at least partially isolated macromolecules from the sample ablation plume to further isolate or partially purify the macromolecules. Extracting macromolecules from an ablation plume can be achieved, for example, by applying an electric field to the ablation plume, such as with the use of one or more electrodes, as described in more detail below. Alternatively, the macromolecules can be extracted from the plume by other methods, such as by hydrodynamic flow processes.

In certain embodiments provided by the present disclosure, the method comprises ablating a biological specimen in an ambient environment with a pulsed laser beam to produce a plume comprising nucleic acids together with an associated plume matrix. A first or substrate electrode is used to direct the ablation plume towards a second or drift electrode, which extracts the nucleic acids from the plume. The extracted nucleic acids can be further transported into a capture device using a third or focusing electrode. In one embodiment, the extracted nucleic acids are focused through an orifice in the drift electrode with a focusing electrode, and captured in a container, such as a polymerase chain reaction (PCR) tube or microfluidic platform, for subsequent amplification and identification, or for further analysis.

In certain embodiments provided by the present disclosure, the method and apparatus include the use of a plurality of separate capture containers for the collection of macromolecules from respective plume ablation locations. In certain embodiments, the capture containers can be provided on a cassette with a movable stage adjacent the laser for the separate capture of hundreds or thousands of macromolecular samples, e.g., nucleic acids, from unique addressable locations on the same sample, or from different samples. Due to the small size of each sample required for identification (e.g., nano-sequencing or mass spectral analysis), the capture containers can be formatted as high-throughput micro-wells or micro-fluidic plates. In certain embodiments, the capture containers are liquid droplets. In certain embodiments, a central processing unit can be used to track the identity of each sample at an addressable location, and to generate from the resulting database a two-dimensional or three-dimensional image of the genomic and/or metabolomic map of a particular specimen.

According to at least one embodiment of the presently disclosed inventive concepts, an apparatus is also provided for sampling and extracting at least partially purified macromolecules of interest from a biological specimen. The apparatus has a sampling component that is configured to project a beam of photons onto a biological specimen to form an ablation plume comprising the macromolecules of interest and a plum matrix. The apparatus further comprises an extraction component to direct the macromolecules of interest from the ablation plume, comprising one, two or three, or more, electrodes configured to capture the macromolecules from the ablation plume. Where the macromolecules are nucleic acids, the apparatus can also comprise an identification component for analyzing the nucleic acids, such as but not limited to PCR amplification, restriction fragment length polymorphism (RFLP) profiling, short tandem repeats (STR) analysis, amplified fragment length polymorphism (AmpFLP) techniques, or metagenome sequencing.

As noted above, the presently disclosed inventive concepts are directed to devices and methods for sampling macromolecules of interest from a biological specimen for capture and identification, said methods comprising sampling the macromolecules by applying a beam of photons to a biological specimen to produce a plume comprising the macromolecule of interest; extracting the macromolecule of interest from the plume; and capturing the extracted macromolecules of interest for detection and analysis. In certain embodiments, the macromolecules of interest are nucleic acids, such as DNA or RNA. In other embodiments, the macromolecules of interest are peptides or proteins, carbohydrates, lipids or other macromolecules (e.g., lipopolysaccharides, lipoproteins, glycoproteins, etc.).

The biological specimen of the present disclosure can be selected from the any material that contains macromolecules, such as nucleic acids, including the group consisting of bacteria, viruses, archaea, fungi, algae, mammalian cells, plant cells, biofilms, plant tissue, animal tissue, human tissue, blood, saliva, hair, urine, tears, semen, other bodily secretions, biology-derived deposits, and combinations thereof. In certain embodiments, the biological specimen can comprise less than 10,000 cells, 1,000 cells, 100 cells, 10 cells, or a single cell. In certain embodiments, the biological specimens can be presented on solid or porous surfaces (such as a filter), and can be either wet or dry. Macromolecules from the biological specimen can also be sampled from a liquid hanging droplet.

In certain embodiments of the presently disclosed method and apparatus for sampling macromolecules of interest, the beam of photons is a laser beam, which can be a pulsed laser beam. The presently disclosed inventive concepts include embodiments wherein the laser beam can have a wavelength selected from the group consisting of infrared wavelengths, visible wavelengths, and ultraviolet wavelengths. According to some embodiments of the presently disclosed inventive concepts, the beam of photons is focused onto the biological specimen using a focusing device, which can be, for example, a mirror, a lens, or an optical fiber. In certain embodiments, the ablation plume is generated by applying energy to the biological specimen by alternative methods such as shock waves or rapid heating.

A laser is a device that emits photon energy through a process of optical amplification based on the stimulated emission of electromagnetic radiation. In laser ablation for example, a small volume of material at the surface of a work piece can be evaporated if it is heated in a very short time. When ablating hydrated biological materials, such as biofilms or tissues, for example, in an atmospheric pressure environment with a laser wavelength of about 3 µm and a fluence (laser pulse energy per unit sample area) that is in the range of 1 J/cm2, the ablation plume typically grows to the size of 2-3 mm in diameter before expansion stops. The laser can be programmed for ablation of a plurality of discrete depths and locations of the biological sample, so as to allow the generation of a generic image of the locations of the macromolecules of interest.

In certain embodiments, a subsequent beam or multiple beams of photons, such as provided by a plurality of pulsed laser beams, can be configured to irradiate the ablation plume created by the first laser beam to dissociate molecular clusters and remove at least some of the plume matrix from the macromolecules of interest. The subsequent photon energy beams can be applied to the ablation plume before, during, or after extraction of macromolecules with electric fields as described below.

In the sampling methods of the present disclosure whereby the macromolecules of interest are extracted from the plume with an electric field, the motion and capture of the macromolecules after their extraction from the ablation plume is also controlled by the application of one or more electric fields. In further embodiments, electric field lines extend from the ablation plume to the point of collection of the macromolecules of interest such as in the bottom of a PCR tube or cuvette. In yet a further embodiment, the electric potential at the collection site is higher than the electric potential in the plume, such that negatively charged nucleic acids are preferentially extracted and captured from the remaining ablation plume matrix material.

By the presently disclosed inventive concepts, in certain embodiments the application of an electric field in the ablation plume, negatively charged macromolecules, such as nucleic acids, are extracted from neutral or positively charged material, in the plume matrix. When the macromolecules of interest are present in the plume as clusters with other molecules, the cluster may have either a positive or a negative charge. Furthermore, by the presently disclosed inventive concepts, the application of an electric field in the ablation plume, macromolecules, such as nucleic acids, can be extracted over lower molecular weight material, including many PCR inhibitors, in the plume matrix.

In certain embodiments of the presently disclosed inventive concepts, sampling methods are provided wherein the transport of the macromolecules of interest is controlled by electric fields and electric potentials which may each vary independently during the time of macromolecule transport to a collection device. In certain embodiments, the electric field is generated using an assembly of electrodes and the extraction device is adjacent to the biological specimen. The presently disclosed inventive concepts provide in certain embodiments, an extraction device including a substrate electrode, a drift electrode, and a focusing electrode. In certain embodiments, the biological specimen has a sampling side and a backside which is opposite of the sampling side. In such embodiments, the substrate electrode can be positioned on the backside of the biological specimen, the drift electrode above the sampling side of the specimen, and the focusing electrode can be positioned on the sampling side and opposite the drift electrode. In a further embodiment, the electric field lines originating in the plume pass through an orifice in the drift electrode.

In certain embodiments of the present disclosure, the method of extracting macromolecules further comprises applying a first voltage or potential to the substrate electrode, a second voltage or potential to the drift electrode, and a third voltage or potential to the focusing electrode. In certain embodiments, the first voltage is 0 volts, the second voltage is within the range of 200 to 1000 volts, and the third voltage is within the range of 2000 to 6000 volts.

In certain embodiments, the presently disclosed inventive concepts include methods wherein the extraction device adjacent to the biological specimen further includes a macromolecule capture container configured to capture the extracted macromolecules of interest. In yet a further embodiment, the electric field lines originating in the plume, enter the container, and reach the inner wall of the container. The container may further consist of an electrically insulating material. In further embodiments, the electric field lines pass through the wall of the electrically insulated container and reach the focusing electrode. In certain embodiments, the macromolecule capture container has surface properties conducive to performing a polymerase chain reaction therein.

According to some embodiments of the presently disclosed inventive concepts, the method and device comprise an extraction device that includes a container consisting of an electrically insulating material wherein the inner walls of the container are restricted to charge densities below the critical value above which the electric field lines that originate in the plume would exit the container. In further embodiments, the surface charge densities are kept below the critical value by limiting the amount of charge that enters the collection container. In certain embodiments, the charge densities are kept below the critical value by maintaining a sufficient surface conductivity of the electrically insulating inner walls of the container. The sufficient surface conductivity may be maintained in certain embodiments by the application of a conducting layer on the inner surfaces of the container. In certain embodiments, the conducting surface layer is applied by water from the ambient environment by maintaining the relative humidity of the gas inside the container above a minimum value that is about 50%, or about 70% relative humidity.

In certain embodiments, the presently disclosed inventive concepts provide a method of extracting nucleic acids from a biological specimen, wherein the method comprises ablating the biological specimen with a pulsed laser beam to produce an ablation plume comprising the nucleic acids together with associated matrix; directing the ablation plume with a first electrode towards a second electrode; extracting the nucleic acids from the ablation plume with the second electrode; focusing the transport lines of extracted nucleic acids through an orifice in the second electrode with a third electrode; and capturing the extracted nucleic acids in a PCR-suited sample holder, such as a tube or microfluidic platform.

In a further embodiment of the present disclosure, said method of extracting nucleic acids comprises applying a first voltage or electric potential to the first electrode, a second voltage or electric potential to the second electrode, and a third voltage or electric potential to the third electrode, wherein the first voltage or electric potential is lower than the second voltage or electric potential, and the second voltage or electric potential is lower than the third voltage or electric potential. In another embodiment, the first voltage or electric potential is higher than the second voltage or electric potential, which is higher than the third voltage or electric potential. In yet a further embodiment, the first electrode is positioned on the backside of the biological specimen, and the second electrode is positioned on the front side of the biological specimen.

Certain embodiments of the presently disclosed inventive concepts include an apparatus for extracting macromolecules of interest from a biological specimen, said apparatus comprising: (a) an ablation laser configured to ablate the biological specimen with a pulsed laser beam to produce an ablation plume comprising macromolecules; and (b) a first, a second, and a third electrode configured to extract the macromolecules from the ablation plume. A further embodiment comprises a container configured to receive the extracted nucleic acids, wherein at least a part of the container is positioned adjacent to or within the third electrode. The apparatus may further comprise a component for amplifying the nucleic acids of interest for identification.

The present disclosure also includes certain embodiments of the apparatus for extracting nucleic acids from a biological specimen, wherein the third electrode is positioned adjacent the second electrode and is configured such that the nucleic acids extracted from the plume through an orifice in the second electrode and/or third electrode. In such cases, the apparatus may have a second electrode configured as a disk with an aperture therethrough (e.g., similar in shape to a washer), and a third electrode located behind the capture tube.

Certain embodiments of the present inventive disclosure include an apparatus for extracting nucleic acids further comprising a lens configured to focus the pulsed laser beam onto the biological specimen, or a mirror, or an optical fiber configured to direct the pulsed laser beam onto the biological specimen. In certain embodiments, the presently disclosed inventive concepts provide that Laser Ablation for Nucleic Acid Recovery (LANAR) rapidly delivers high quality, at least partially inhibitor- and contaminant-free, at least partially isolated nucleic acids, for associated PCR amplification or metagenome sequencing.

In certain embodiments of the inventive disclosure, the method and apparatus comprise a second laser, or plume laser, configured to irradiate the ablation plume. In certain embodiments, the subsequent plume laser is pulsed or steady and can follow the first laser ablation by 10 to 100 µs. The plume laser further removes at least some of the plume matrix material from the macromolecules of interest. The subsequent plume laser application can occur before or during the electronic field created by the substrate electrode, drift electrode, and/or focusing electrode.

In some embodiments of the presently disclosed inventive concepts, the apparatus has one or more electric fields which focus and/or direct macromolecules of interest into a container or sample inlet in a device for analysis. The electric fields can be constant or pulsed. Generally speaking, an electric field, such as one with focusing properties, can be produced with a range of electrode configurations. To this end, the electric field can be configured such that it is suitable for directing and focusing the transport of macromolecules of interest, which may be one or more charged or ionized macromolecules. In certain situations, the macromolecules of interest are naturally charged prior to laser ablation. In cases where the macromolecules are not charged or are not sufficiently charged, the laser ablation apparatus may include a component for ionizing the sample so as to produce a charge suitable for focusing, directing and/or capturing the macromolecules by one or more electric fields. Alternatively, a substance may be introduced into the sample or into the ablation plume so as to associate with the macromolecule of interest and impart a charge to facilitate focusing, directing, and or capturing the macromolecules.

In at least one embodiment, a first and a second electrode in the LANAR apparatus is configured to extract the macromolecule of interest from the ablation plume. In other embodiments, a first and a second electrode is provided for extracting the macromolecule of interest from an ablation plume, and a third electrode is provided for focusing the electrophoretic transport of extracted macromolecules. In some embodiments, the extraction portion of the LANAR device includes a substrate electrode, a drift electrode and a focusing electrode. In certain cases, the drift electrode is positioned between a biological specimen and the focusing electrode. In some embodiments, the first and second electrodes are adjacent to one another. In addition, alternative configurations are possible. In an exemplary embodiment, the third electrode may be configured to focus the electrophoretic transport of macromolecules extracted from the plume. The second electrode may also have an opening through which the third electrode focuses the flow of macromolecules of interest. In some cases, a container for receiving the macromolecule of interest may be positioned within or adjacent to the third electrode. In some embodiments, the electrodes are shaped so as to support the focusing and extracting function of the apparatus, such as a second electrode comprising a washer and a third electrode comprising a tube.

In some exemplary embodiments, the method for extracting the macromolecule may include applying a first voltage to a drift electrode relative to a substrate electrode, and a second voltage to a focusing electrode relative to the substrate electrode. In some cases, the first voltage is less than the second voltage, such as a first voltage in a range of about 200 to about 1000 volts and a second voltage in a range of about 2000 to about 6000 volts. As such, the apparatus may have first, second and third electrodes wherein first and second voltages of different ranges may be applied thereto. In some cases, the substrate electrode is electrically grounded.

Certain non-limiting embodiments of the LANAR apparatus may also include other elements and features that facilitate focusing of the laser ablation beam onto the specimen. For instance, the apparatus may include a lens, an optical fiber and/or a mirror that are configured to direct and/or focus a pulsed laser beam onto a specimen. The apparatus may include subsequent laser beams to dissociate molecular clumps to separate plume matrix from macromolecules of interest. Embodiments may also include a dish for holding a biological specimen that is specifically designed to facilitate extracting the macromolecule of interest. The shape and/or material of the dish may have particular importance in some embodiments. For instance, materials that do not degrade the sample, but also allow release of the macromolecule may be desirable. Furthermore, the ability to regulate the temperature, humidity or other environmental variable of the sample may be important in some cases, such as where the specimen is unstable under certain conditions. In some cases, the dish may be configured so as to facilitate the specimen ablation, and extraction and capture of macromolecules of interest from flat as well as three-dimensional substrates, such as glass wool and woven fabrics. Furthermore, dry as well as liquid samples may be accommodated in exemplary embodiments.

EXAMPLES

By means of certain embodiments of the methods and apparatus herein described, macromolecules of interest, such as nucleic acids, are collected within a minute, or even a few seconds, by irradiating cells with a pulsed, mid-IR laser beam under ambient conditions. An electrode system guides at least some of the ablated macromolecules directly into a PCR tube, and thus, for example, collected nucleic acids are ready for polymerase chain reaction (PCR) amplification, as is represented in FIG. 1. FIG. 1 shows a sectional view of an exemplary Laser Ablation for Nucleic Acid Recovery (LANAR) apparatus including: a) path of incident, pulsed laser beam; b) substratum (substrate electrode) with a loaded sample; c) extraction electrode; d) cylindrical shielding skirt; e) tubular focusing electrode; f) electrical connection post for focusing electrode; and g) 0.5 mL PCR tube. Owing to its speed, simplicity and nucleic acid recovery from nano and sub-nanoliter volumes of material, LANAR offers not only in- or ex-situ diagnostics of biological contamination, but can also pioneer genomic 3-D imaging of target organisms within a biofilm/tissue and/or entire biofilm community structure.

The presently disclosed inventive concepts provided in certain embodiments can be used to recover, in less than one minute, nucleic acid fragments of at least 0.6 kb size from intact, either wet or dry, bacterial cells. In certain embodiments, the nucleic acids can be amplified by a component of the apparatus in the field at the sampling location for rapid mobile identification of the organism harboring the nucleic acid.

Figure 2:
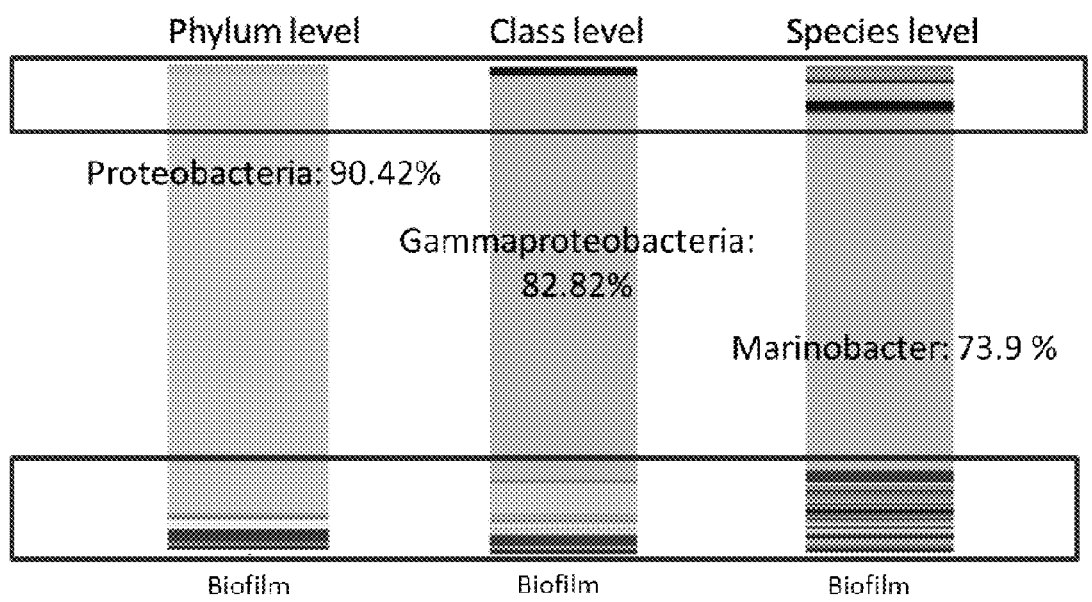
FIG. 2 represents identification sequences of LANAR-harvested DNA from 3 weeks-old marine biofilm grown on the surface of 1018 carbon steel exposed to as-received Key West seawater, seeded with *Marinobacter* isolate B1, and overlaid with JP5 naval fuel.

The presently disclosed inventive concepts provide in certain embodiments that macromolecules of interest can be ablated and captured for identification from a wide variety of planar and three-dimensional substrates. For example, harvesting of macromolecules such as nucleic acids from aerobic Gram-positive *Bacillus* spp. and anaerobic Gram-negative sulfate-reducing bacterium of the genus *Desulfoglaeba* deposited on a number of insulating (wood, plastic, glass, textile such as a piece of cloth from the US army uniform) or conducting (copper, carbon steel, silicon wafer) surfaces has been demonstrated. Nucleic acids can be ablated after binding to antibody-coated surfaces. Nucleic acids can also be collected directly from selected areas of live marine biofilms thriving on 1018 carbon steel surfaces. The ablated nucleic acids do not require additional processing prior to PCR and is of high purity, as verified by the quality of the PCR product sequences. In some embodiments, only a few cells per ablated area are needed to achieve successful DNA recovery, regardless of the substratum. The presently disclosed inventive concepts herein described in certain embodiments preserve high-quality DNA during the ablation process, while minimizing the co-sampling of PCR-inhibiting compounds, as evidenced by successful sequencing of LANAR harvested biofilm DNA (FIG. 2). FIG. 2 represents identification sequences of LANAR-harvested DNA from 3 weeks-old marine biofilm grown on the surface of 1018 carbon steel exposed to as-received Key West seawater, seeded with *Marinobacter* isolate B1, and overlaid with JP5 naval fuel.

In certain embodiments, the laser beam may be selected from lasers that emit within a range of wavelengths, including infrared wavelengths, visible wavelengths, and ultraviolet wavelengths. In particular, experiments have been performed with three available beam wavelengths (355 nm, 532 nm, and 2.94 µm) and PCR amplifications of ablated DNA have been successfully demonstrated using all three wavelengths. However, ablation of hydrated samples using the mid-IR 2.94 µm laser beam was found to be particularly successful. Field Emission Scanning Electron Microscopy (FEM) images of 2.94 µm laser-ablated crystalline silicon surfaces onto which a suspension of bacterial cells (*D. alkanexedens* or *B. licheniformis*) had been pipetted are presented in FIG. 3A-3D.

Figure 3A:
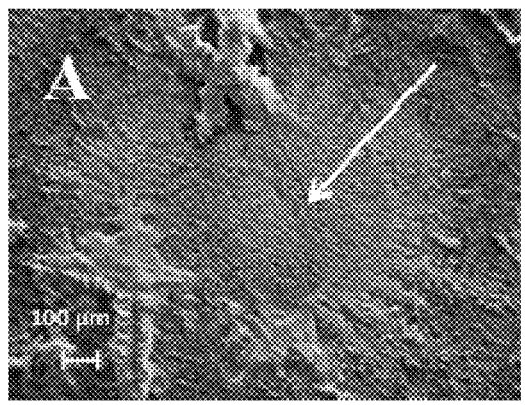
FIGS. 3A-3D provide FEM images of bacterial cells deposited on a crystalline Si surface after irradiation with a pulsed laser beam.
Figure 3B:
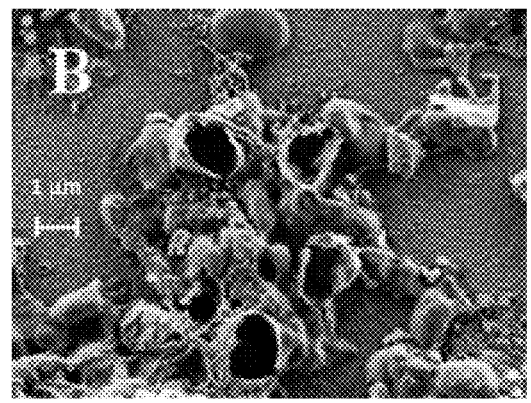
Figure 3C:
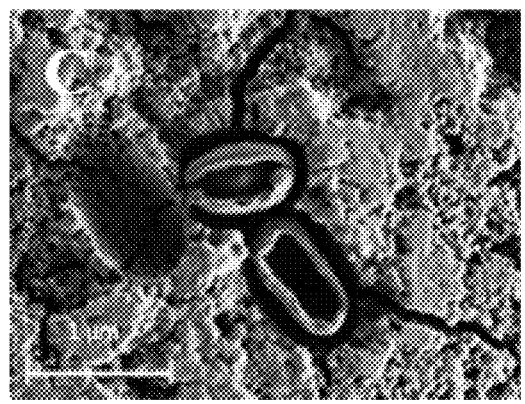
Figure 3D:
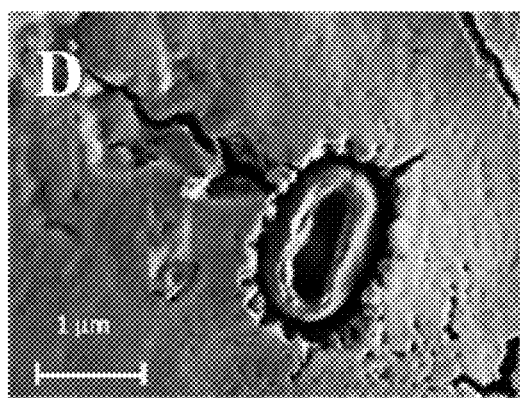

The "gutted" cells observed in FIG. 3B-3D are a characteristic feature of most 2.94 µm laser ablation experiments. It appears that the cell wall fracture and subsequent ejection of cell material is the result of a sudden pressure increase in the superheated cell interior during and immediately after the laser pulse. This process is not very different from what can be observed in the macroscopic world, when vessels are suddenly pressurized.

In certain embodiments of the presently disclosed inventive concepts, when the macromolecules of interest are nucleic acids (DNA or RNA), it may be subjected to polymerase chain reaction analysis. In certain other embodiments, the nucleic acids can be used for metagenomic analysis, with or without PCR. Varieties of polymerase chain reaction (PCR) platforms, such as traditional isothermal, digital and microfluidic are known in the art and may be used for amplifying nucleic acids, including those performing "real time" analysis using quantitative PCR instrumentation.

Collection of macromolecules extracted from ablation plumes into 1.5 ml PCR tubes, followed by successful PCR amplification, were performed under a variety of different experimental conditions, including different sample hydration levels (from "dry" to "wet"), different support substrates (silicon, copper, glass, glass wool, agar, chemical polymers, textile, wood, brick), different sample preparations (direct deposition, sonication, freezing), different bacterial species, different laser frequencies (2.94 μm, 532 nm, and 355 nm), and different laser pulse energies. For example, reliable PCR detection (>95%) was achieved with mid-IR laser irradiation of well-hydrated bacterial samples.

Figure 4A:
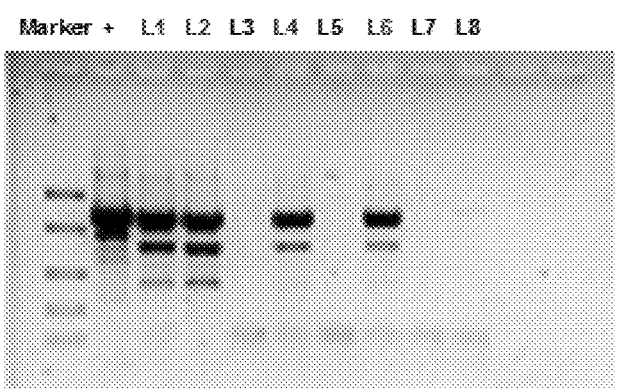
FIGS. 4A-4B provide photographs of agarose gels demonstrating direct PCR amplification of DNA collected from laser-ablated *D. alkanexedens*, using functional primers: AprB1 and AprA5R (FIG. 4A), and laser-ablated *B. licheniformis* cells, using 16S-rRNA primers (FIG. 4B). Positive controls (lane marked +) were *Archaeoglobus* in a) and *E. coli* in b). Samples producing positive results are labeled in red.
Figure 4B:
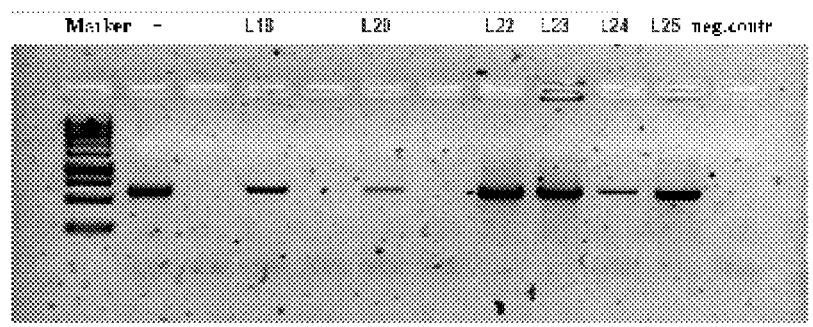

Representative photographs of agarose gels of PCR-amplified DNA, sampled with LANAR are depicted in FIGS. 4A and 4B. For *Desulfoglaeba alkanexedens*, upper gel, the aps primers: AprB1 and AprA5R, were used, while for *Bacillus licheniformis*, lower gel, 16S-rRNA primers were used. PCR products were obtained through direct amplification of DNA from laser ablated *B. licheniformis* cells, using 16S rRNA universal bacterial primers. Identical sequences were obtained from PCR products from LS22, LS23 and LS25 samples (FIG. 4B).

All amplicons contained 588 bp. BLASTN analysis revealed 100% similarity in sequences between LANAR-PCR samples and over 50 *B. licheniformis* strains.

Figure 5A:
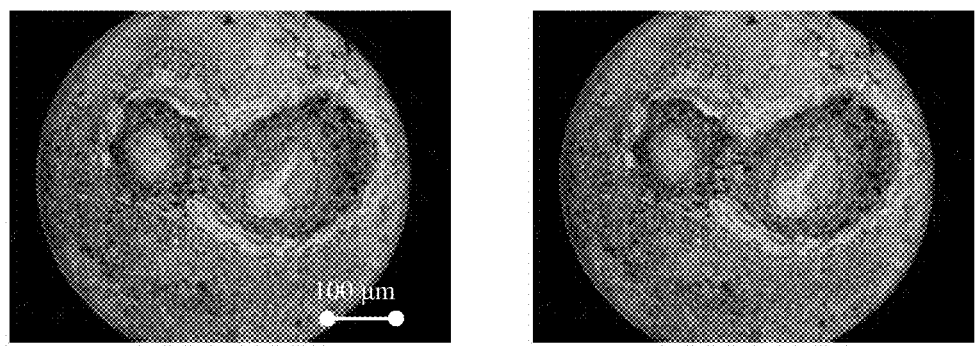
FIGS. 5A-5B show images of laser holes drilled through a 450 μm-thick biofilm and corrosion product layer to reach the 1018 carbon steel substrate by a series of successive, focused 3 μm-wavelength, 2 mJ-energy laser pulses.

The size of the mid-IR laser focus, from which nucleic acids are sampled, can be about 150×100 μm. From hydrated, biological materials, such as tissue or biofilm, each laser pulse ablates material to a depth of approximately 10 μm. Thus, the volume of tissue ablated per laser shot can be about 150 pL, or 0.15 nL. In a typical LANAR procedure, nucleic acids from a series of 20 laser shots were fired in one second; thus, approximately 3 nL of tissue or biofilm was sampled. The 20 laser shots typically "drill" a 200-μm deep hole into the biofilm. FIG. 5A shows images (reconstructed from microscopy images) of two adjacent LANAR sampling locations on a 450 μm-thick biofilm in which the ablation reached the metallic substrate of the biofilm.

Figure 5B:
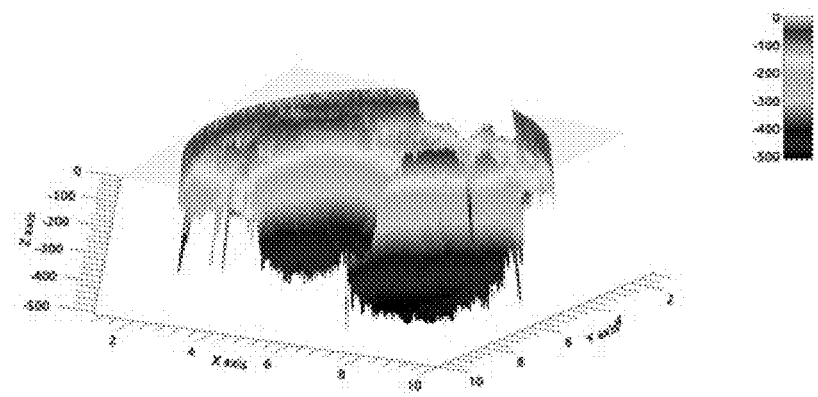

FIGS. 5A-5B show images of laser holes drilled through a 450 μm-thick biofilm and corrosion product layer to reach the 1018 carbon steel substrate by a series of successive, focused 3 μm-wavelength, 2 mJ-energy laser pulses. FIG. 5A shows computer-generated top-view composite image of 20 separate stereomicroscope images obtained at different depths. FIG. 5B shows 3-dimensional contours of the holes generated from the same image data as was used for FIG. 5A.

Figure 5C:
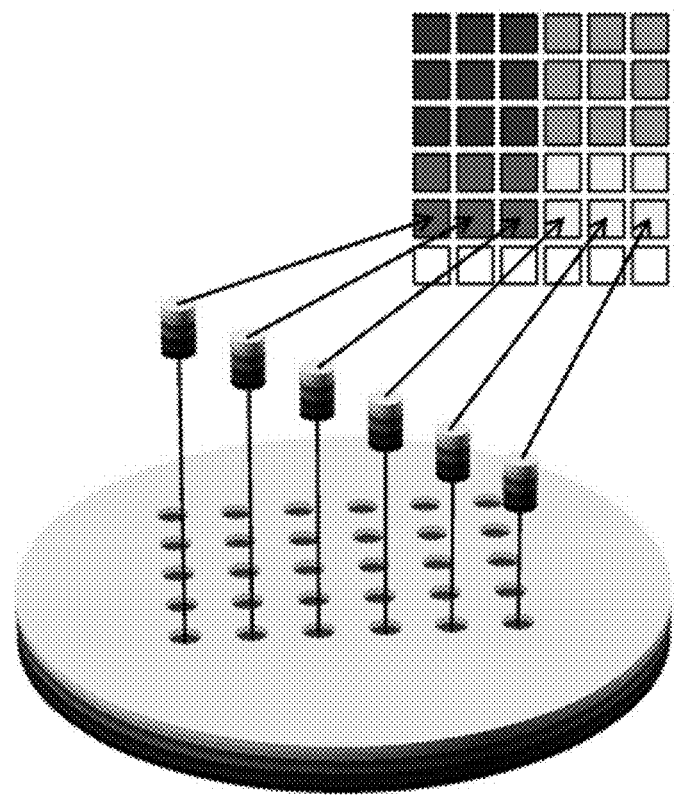
FIGS. 5C-5D show schematics of how LANAR can be used to obtain three-dimensional localized genomic profiles and linear genomic profiles, respectively.
Figure 5D:
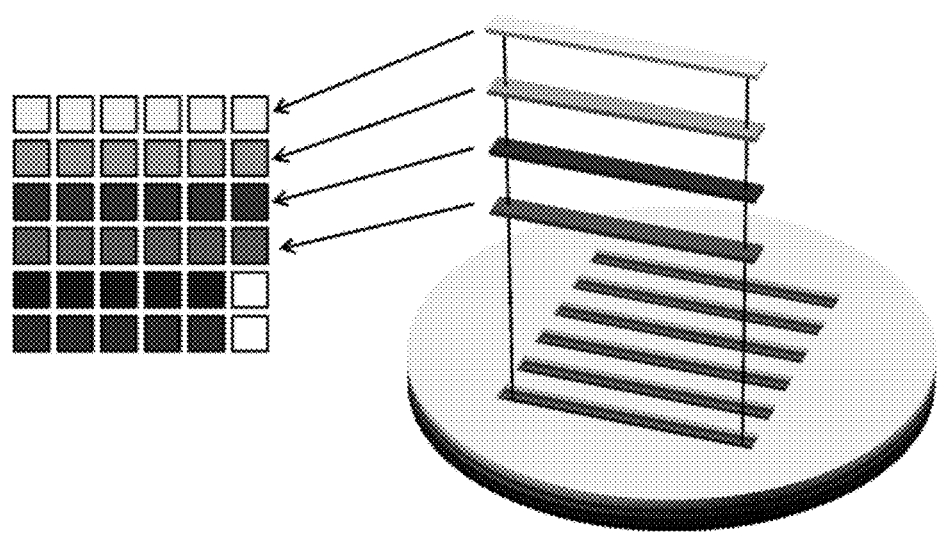

FIGS. 5C-5D show schematics of how LANAR can be used to obtain three-dimensional localized genomic profiles and linear genomic profiles, respectively. In FIG. 5C, repeated laser shots within a selected area penetrate into a biofilm to different depths. DNA is collected from each laser ablated area and subjected to PCR and sequencing. The DNA profiles obtained from each ablated area are processed with designated software to obtain genomic "images" depicting spatial heterogeneity of the biofilm bacterial community. The average size of the laser ablation spot is typically 120-150 micrometers. The ablated volume is approximately 0.00015 μL (150 pL). Alternatively, as shown in FIG. 5D, one laser shot is fired along a length of the selected area, and ablated DNA is collected across the location as the stage or the laser beam moves continuously along an x-axis. The process can be repeated several times at the same location to provide a linear depth profile. The penetration depth of the laser beam can vary with sample type, but typically does not exceed 10 micrometers.

In certain embodiments, both genomic and metabolomic data can be obtained and correlated to provide maximum information. In certain embodiments, the laser ablation plume can be split into separate capture chambers for different analysis. In embodiments, the invention can use an in-plane spatial resolution of about 150 μm and with a spatial resolution of about 10 μm in the depth dimension. When the objective is to determine a genomic depth profile, the shape of the ablated volume can be changed by performing minute motions of the stage during the firing of a few laser pulses for every individual nucleic acid collection event. Moreover, for genomic imaging, an array or a plate that can accommodate multiple samples (100 or more) and is suitable for multichannel PCR can be used to collect nucleic acids from each laser ablated spot.

Figure 6:
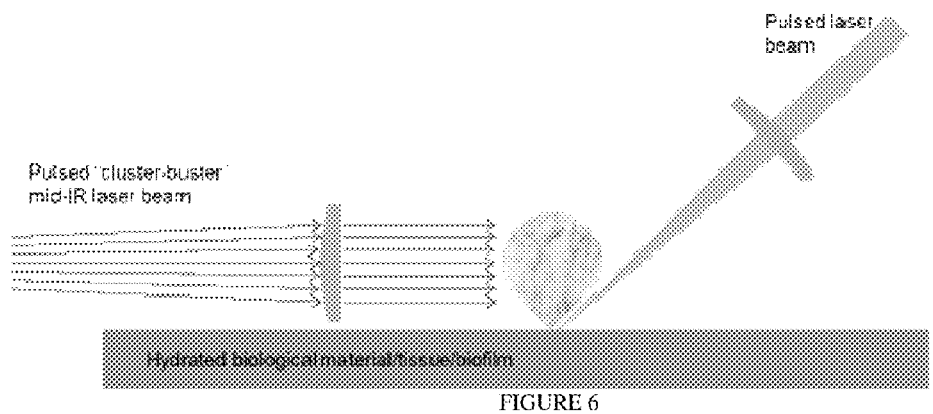
FIG. 6 is a conceptual schematic of the LANAR embodiment where a second pulsed laser beam is applied to the plume generated by the first pulsed laser to dissociate matrix clusters and at least partially isolate macromolecules of interest (not to scale).

FIG. 6 shows that the separation of macromolecules from lower molecular weight matrix in the plume can be further improved by breaking up the clusters using a second pulsed laser beam. In this set-up, the second laser pulse is used to irradiate the whole plume at some point in its development. Thus, it is delayed relative to the ablation laser pulse by 10 to 100 μs, for example. The generation of relatively solvent-free nucleic acids in this way can assist operation of LANAR.

Figure 7:
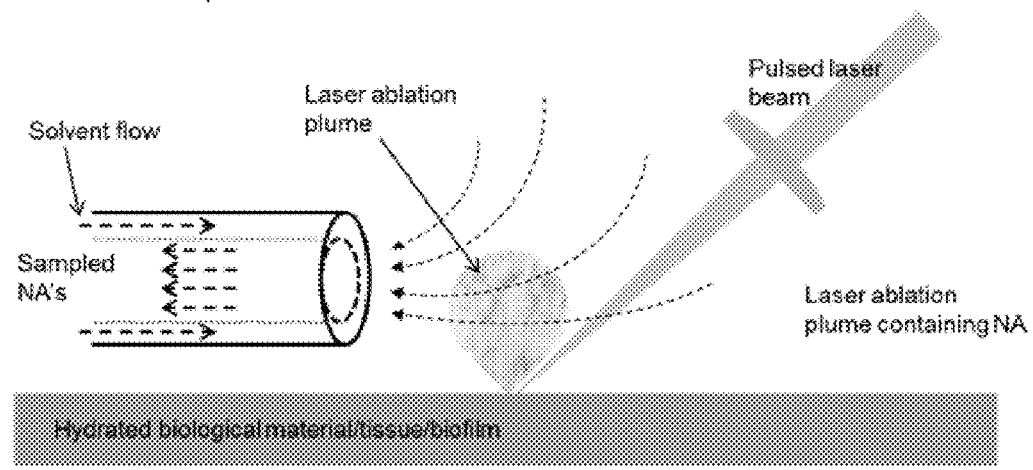
FIG. 7 is a conceptual schematic of the LANAR aspiration interface with collection capillary perpendicular to the direction of plume expansion (not to scale).
Figure 8:
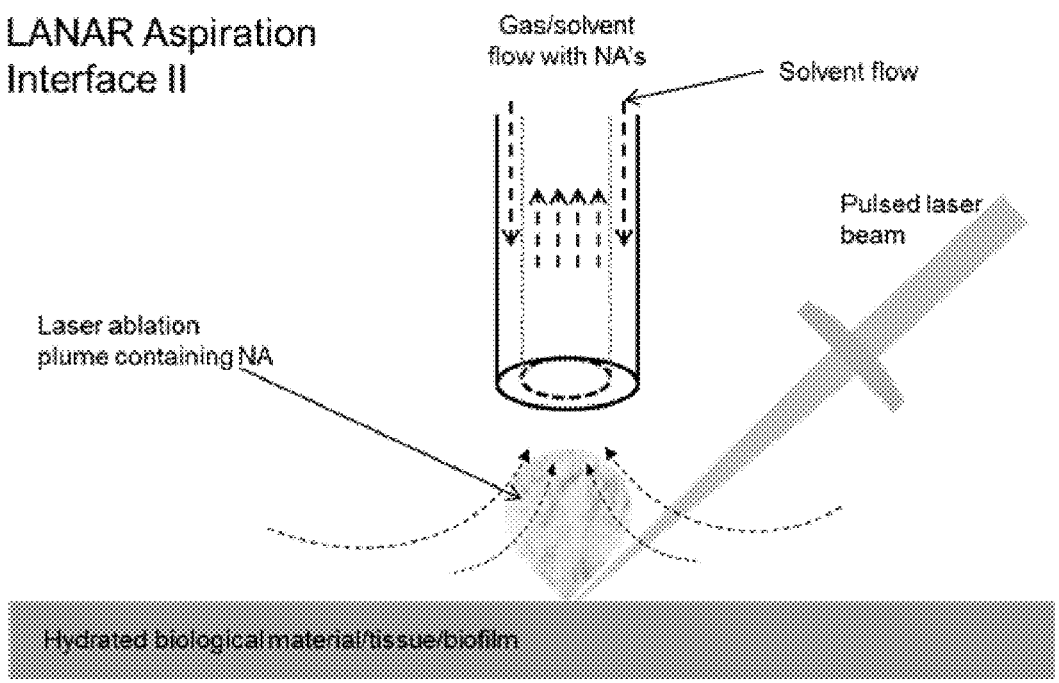
FIG. 8 is a conceptual schematic of LANAR aspiration interface with collection capillary in line with plume expansion direction (not to scale).

In imaging mode, with aspiration collection, ablation plumes generated in each pixel are aspirated into a collection capillary into which simultaneously a flow of solvent is drawn (FIGS. 7 and 8). The choice of solvent depends upon the desired effect in the effluent stream. Typically an aqueous solution is an appropriate solvent. Additional reagents can be added, such as PCR components or solubilization agents. For some applications, such as an electrospray, a solvent mixture can be used, such as water and ethanol. For other applications, such as for isolating trans-membrane proteins, an organic solvent can be used. The interface can be operated under high-flow conditions, which creates a mixed solvent/gas flow in the collection capillary. The orientation of the collection capillary inlet is not critical, but its opening should be located in the immediate vicinity of the laser ablation site.

The aspiration interface, with or without electrophoretic extraction of macromolecules, can be used to collect nucleic acids applying anywhere from a single to a large number of laser shots. Following collection, the solvent containing the nucleic acids can be processed in different ways, for example, it can be channeled directly into PCR tubes using transport capillaries and automatic valves. Materials such as bovine serum albumin (BSA) can be added to minimize nucleic acid adsorption on solid surfaces or other materials to stabilize the sample from degradation. In certain embodiments, the nucleic acids are directed into a microfluidic device, such as one that performs PCR in about 10 minutes.

An aspiration flow interface can also be used to collect nucleic acids in a low-flow mode in which the nucleic acids are adsorbed on a liquid surface and gently drawn into the collection capillary.

Figure 9:
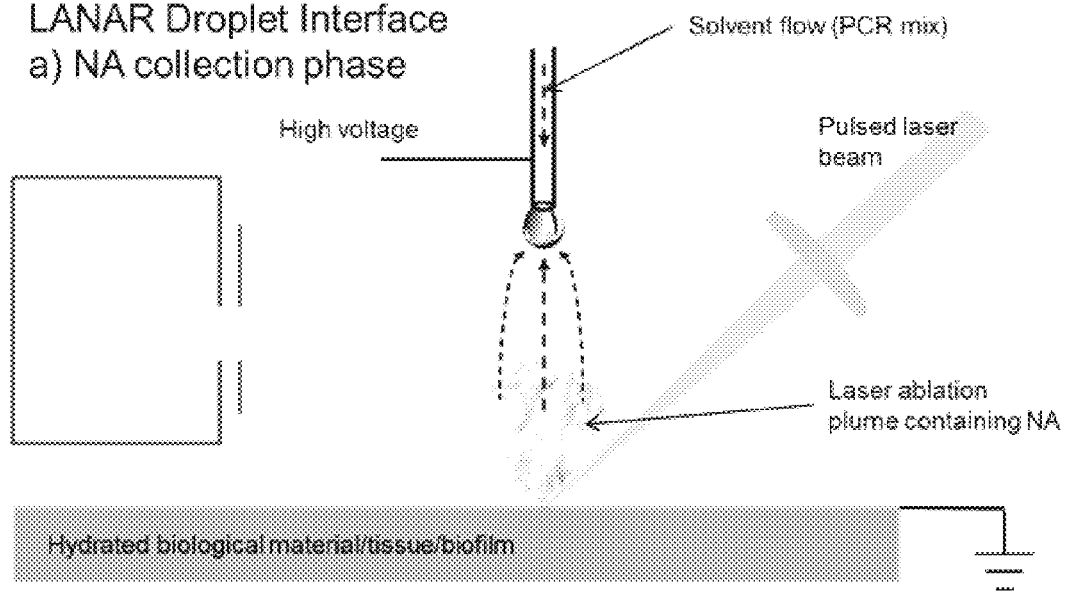
FIG. 9 is a conceptual schematic of LANAR droplet collection interface (not to scale) during electrostatic collection of laser-ablated nucleic acids (nucleic acids).
Figure 10:
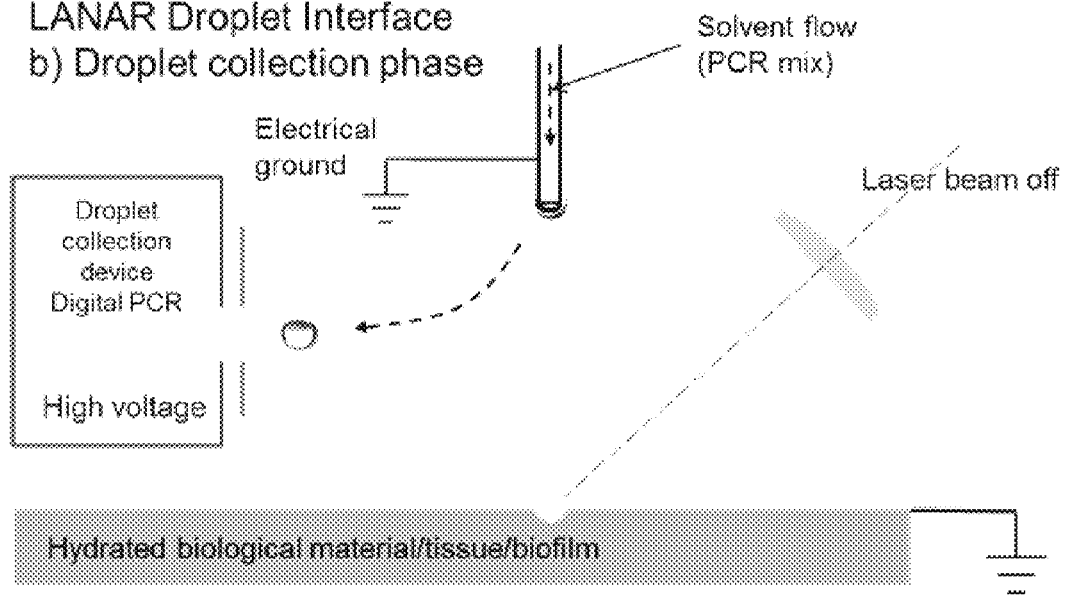
FIG. 10 is a conceptual schematic of LANAR droplet collection interface (not to scale) during electrostatic collection of detached droplet with sampled nucleic acids.

A variety of collection methods may be used for the macromolecules, which include nucleic acids, peptides or proteins, present in the laser ablation plume. In other embodiments, an aspiration interface such as is shown in FIGS. 7 and 8, or a droplet collection interface as represented in FIGS. 9 and 10 can be used. In the various embodiments, the collection methods are configured so as to provide a mechanism for obtaining the laser ablation plume in general, and the macromolecules of interest, in particular, into the sample container, tube, cuvette or a device sample inlet. The container, tube, cuvette or sample inlet may be configured advantageously to capture an extracted macromolecule of interest for identification, such as by PCR amplification or metagenome sequencing, and detection of the macromolecules of interest.

In one embodiment of LANAR, the complete laser ablation plume is sampled, as in the aspiration interfaces shown in FIGS. 7 and 8, while in a different embodiment the macromolecules of interest are first extracted from the plume using an electric field, prior to being sampled with an aspiration interface. The main body of the plume is collected in the opposite direction by a gentle gas flow and either discarded or stored for chemical analysis. A primary advantage of electrophoretic macromolecular extraction is that the macromolecules are at least partially isolated or substantially separated from their biological matrix, i.e. obtained in a more pure state than in their natural state.

In one embodiment of LANAR, electrophoretically extracted macromolecules are sampled into droplets. Sampling into a hanging droplet is illustrated in FIG. 8. In a different embodiment, the macromolecules are collected by much smaller droplets. The collection can be performed both fast (milliseconds) and quantitatively by utilizing electrostatic attraction, i.e. by charging the macromolecules and the collection droplets at opposite polarity. The collection droplets can be formed by a monodisperse aerosol generator to which any reagents, such as those used for PCR can be added. A train of droplets is electrostatically transported through the LANAR interface and into a digital PCR instrument. This embodiment of LANAR allows for hundreds or thousands of PCR analyses to be performed in parallel. Embodiments of LANAR with this capability may be referred to as Digital LANAR.

Nucleic acid molecules are large enough that they will typically acquire a net electric charge during the ablation and electrophoretic separation processes. The sign of the net charge will further be influenced by the direction of the electric field throughout the laser ablation plume. FIG. 9 shows the electrostatic collection of nucleic acids onto a hanging droplet. An electric field can be created between the sample and the droplet by grounding the sample support and applying a high voltage, usually positive and about 1,000 V, to the droplet. In certain embodiments the droplet is withdrawn into the capillary. However, in other embodiments it may be efficient to detach the droplet, by electrostatics or by mechanical vibrations, and then send the droplet to a sampling device, see FIG. 10.

LANAR sampling into droplets is well-suited for direct interfacing with digital PCR, i.e., the performance of PCR in a large number of very small droplets. This approach is particularly suitable for quantitative PCR. By means of the exemplary embodiments that are representatively illustrated herein, the specific detection of targeted microbial species (such as pathogens) in a large number of locations or for species-specific imaging in tissue and/or biofilms is made possible.

Both aspiration- and droplet-based LANAR collection can be interfaced to different types of microfluidic devices that perform PCR. Furthermore, by interfacing a LANAR apparatus with portable, and hand-held, analyzers, the real time, on location analysis of nucleic acids and other macromolecules of interest is made possible.

As can be appreciated in view of the disclosure, the methods and apparatus of the present concept can be used in an exceedingly wide range of analytical applications, including but not limited to biohazard detection, analysis of microbial biofilms on a wide range of metallic and non-metallic materials, food and drink contamination detection, water and air quality inspection (via filtration), and diagnosis of infectious agents in bodily fluids, in human, animal and plant tissues, and on bodily implants for targeted therapeutic treatment.

It will be understood from the foregoing description that various modifications and changes may be made in the various embodiments of the present disclosure without departing from their true spirit. The description provided herein is intended for purposes of illustration only and is not intended to be construed in a limiting sense. Thus, while the presently disclosed inventive concepts have been described herein in connection with certain embodiments so that aspects thereof may be more fully understood and appreciated, it is not intended that the presently disclosed inventive concepts be limited to these particular embodiments. On the contrary, it is intended that all alternatives, modifications and equivalents are included within the scope of the presently disclosed inventive concepts as defined herein. Thus the examples described above, which include particular embodiments, will serve to illustrate the practice of the presently disclosed inventive concepts, it being understood that the particulars shown are by way of example and for purposes of illustrative discussion of particular embodiments of the presently disclosed inventive concepts only and are presented in the cause of providing what is believed to be a useful and readily understood description of procedures as well as of the principles and conceptual aspects of the inventive concepts. Changes may be made in the construction and formulation of the various components and compositions described herein, the methods described herein or in the steps or the sequence of steps of the methods described herein without departing from the spirit and scope of the presently disclosed inventive concepts.

REFERENCES (1) Lin, Z.; Cai, Z. Cell lysis methods for high-throughput screening or miniaturized assays. *Biotechnology Journal* 2009, 4, 210-215.

(2) Kephart, D.; Krueger, S.; Grunst, T.; Shenoi, H. Introducing the Maxwell® 16 Instrument: A simple, robust and flexible tool for DNA purification. *Promega Notes* 2006, 92, 20-23.

(3) Chomczynski, P.; Rymaszewski, M. Alkaline polyethylene glycol-based method for direct PCR from bacteria, eukaryotic tissue samples, and whole blood. *BioTechniques* 2006, 40, 454-458.

(4) Zoetendal, E. G.; Ben-Amor, K.; Akkermans, A. D. L.; Abee, T.; de Vos, W. M. DNA isolation Protocols affect the detection limit of PCR approaches of bacteria in samples from the human gastrointestinal tract. *Syst. Appl. Microbiol.* 2001, 24, 405-410.

(5) Schrader, C.; Schielke, A.; Ellerbroek, L.; Johne, R. PCR inhibitors—occurrence, properties and removal. *J. Appl. Microbiol.* 2012, 113, 1014-1026.

(6) Wilson, I. G. Inhibition and facilitation of nucleic acid amplification. *Appl. Environ. Microbiol.* 1997, 63, 3741-3751.

(7) Hynes, W. L.; Ferretti, J. J.; Gilmore, M. S.; Segarra, R. A. PCR amplification of streptococcal DNA using crude cell lysates. *FEMS Microbiol. Lett.* 1992, 94, 139-142.

(8) Radstrom, P.; Knutsson, R.; Wolffs, P.; Lovenklev, M.; Lofstrom, C. Pre-PCR processing—Strategies to generate PCR-compatible samples. *Mol. Biotechnol.* 2004, 26, 133-146.

(9) Dhawan, M. D.; Wise, F.; Baeumner, A. J. Development of a laser-induced cell lysis system. *Anal. Bioanal. Chem.* 2002, 374, 421-426.

(10) Rau, K. R.; Quinto-Su, P. A.; Hellman, A. N.; Venugopalan, V. Pulsed laser microbeam-induced cell lysis: Time-resolved imaging and analysis of hydrodynamic effects. *Biophys. J.* 2006, 91, 317-329.

(11) Brown, R. B.; Audet, J. Current techniques for single-cell lysis. *Journal of the Royal Society Interface* 2008, 5, S131-S138.

(12) Tanaka, K.; Waki, H.; Idao, Y.; Akita, S.; Yoshida, Y.; Yoshida, T. Protein and polymer analyses up to m/z 100,000 by laser ionization time-of-flight mass spectrometry. *Rapid Communications in Mass Spectrometry* 1988, 2, 151-153.

(13) Karas, M.; Bachmann, D.; Bahr, U.; Hillenkamp, F. Matrix-assisted ultraviolet laser desorption of non-volatile compounds. *IJMSIP* 1987, 78, 53-68.

(14) Ovchinnikova, O. S.; Bhandari, D.; Lorenz, M.; Van Berkel, G. J. Transmission geometry laser ablation into a non-contact liquid vortex capture probe for mass spectrometry imaging. *Rapid Communications in Mass Spectrometry* 2014, 28, 1665-1673.

The following are considered to be exemplary and not exhaustive of embodiments of the inventive concepts of the present disclosure which may be claimed and are not intended to be limiting of the embodiments which may be claimed in a subsequent application.

We claim:

1. A method of sampling macromolecules of interest directly from a biological specimen for capture and identification, comprising:
   (a) applying a laser beam of photons to the biological specimen to produce an ablation plume comprising a plume matrix and the macromolecules of interest at least partially isolated from the biological specimen;
   (b) extracting the macromolecules of interest from the plume matrix with an electric field; and
   (c) capturing the extracted macromolecules of interest in a container for analysis, wherein electric field lines extend from the plume to the container, and wherein an electric potential at the container is higher than the electric potential in the ablation plume, such that negatively charged macromolecules are preferentially extracted from the plume matrix as the macromolecules of interest; and wherein the electric field is established by a substrate electrode, a drift electrode and a focusing electrode, and wherein extracting the macromolecules of interest is controlled by increasing the potential of electric fields among the electrodes toward the container.

2. The method of claim 1, wherein the biological specimen is situated in an ambient environment.

3. The method of claim 1, in which the negatively charged macromolecules of interest are nucleic acids.

4. The method of claim 3, further comprising subjecting the extracted nucleic acids to polymerase chain reaction analysis or metagenome sequencing methods.

5. The method of claim 1, in which the negatively charged macromolecules of interest have a molecular weight of 1,000 Dalton or higher.

6. The method of claim 1, wherein the laser beam is a pulsed laser beam.

7. The method of claim 1, wherein the beam of photons is focused onto the specimen using a focusing device, wherein the focusing device is a mirror, lens or optical fiber.

8. The method of claim 1, wherein the biological specimen is selected from the group consisting of bacteria, viruses, archaea, fungi, biofilms, plant tissue, animal tissue, human tissue, blood, saliva, hair, urine, bodily secretions, and combinations thereof.

9. The method of claim 1, wherein the biological specimen is present on a three-dimensional surface.

10. The method of claim 1, wherein the biological specimen has a sampling side and a backside which is opposite of the sampling side, wherein the substrate electrode is positioned on the backside of the biological specimen, the drift electrode is positioned above the sampling side of the specimen, and the focusing electrode is positioned on the opposite side of the drift electrode from the biological specimen.

11. The method of claim 10, wherein electric field lines originating in the plume pass through an orifice in the drift electrode.

12. The method of claim 10, wherein the extracting is achieved by applying a first voltage to the substrate electrode, applying a second voltage to the drift electrode wherein the second voltage is higher than the first voltage, and applying a third voltage to the focusing electrode wherein the third voltage is higher than the second voltage.

13. A method of extracting nucleic acids of interest from a biological specimen, said method comprising:
   (a) ablating the biological specimen with a pulsed laser beam to produce an ablation plume comprising the nucleic acids together with associated plume matrix;
   (b) directing the ablation plume with a first electrode towards a second electrode;
   (c) extracting the nucleic acids from the ablation plume with the second electrode to form transport lines of extracted nucleic acids;
   (d) focusing the transport lines of extracted nucleic acids through an orifice in the second electrode with a third electrode; and
   (e) capturing the extracted nucleic acids in a container suitable for conducting a polymerase chain reaction.

14. The method of claim 13, further comprising applying a first voltage or first electric potential to the first electrode, a second voltage or second electric potential to the second electrode, and a third voltage or third electric potential to the third electrode, wherein the first voltage or first electric potential is lower than the second voltage or second electric potential, and the second voltage or second electric potential is lower than the third voltage or third electric potential.

15. The method of claim 13, further comprising applying a first voltage or first electric potential to the first electrode, a second voltage or second electric potential to the second electrode, and a third voltage or third electric potential to the third electrode, wherein the first voltage or first electric potential is higher than the second voltage or second electric potential, and the third voltage or third electric potential is higher than the second voltage or second electric potential.

16. An apparatus for extracting macromolecules from a biological specimen, said apparatus comprising:
   (a) a laser configured to ablate the biological specimen with a pulsed laser beam to produce an ablation plume comprising the macromolecules; and
   (b) a first electrode, a second electrode, and a third electrode configured to extract the macromolecules from the ablation plume,
   wherein the apparatus is configured to perform a method of sampling the macromolecules of interest directly from the biological specimen for capture and identification, comprising:
      (i) applying the laser beam of photons to the biological specimen to produce the ablation plume further comprising a plume matrix and the macromolecules of interest at least partially isolated from the biological specimen;

(ii) extracting the macromolecules of interest from the plume matrix with an electric field; and (iii) capturing the extracted macromolecules of interest in a container for analysis, wherein electric field lines extend from the plume to the container, and wherein the electric potential at the container is higher than the electric potential in the ablation plume, such that negatively charged macromolecules are preferentially extracted from the plume matrix as the macromolecules of interest; and wherein the first electrode, the second electrode, and the third electrode, are a substrate electrode, a drift electrode and a focusing electrode, respectively, establishing the electric field, wherein extracting the macromolecules of interest is controlled by increasing the potential of electric fields among the electrodes toward the container.

17. The apparatus of claim 16, wherein the third electrode is positioned adjacent the second electrode and configured such that the negatively charged macromolecules extracted from the plume pass through an orifice in the second electrode.

18. The apparatus of claim 16, in which the negatively charged macromolecules of interest are nucleic acids.

19. The apparatus of claim 16, in which the negatively charged macromolecules of interest have a molecular weight of 1,000 Dalton or higher.

20. The apparatus of claim 16, wherein the beam of photons is focused onto the specimen using a focusing device, wherein the focusing device is a mirror, lens or optical fiber.

* * * * *